(12) United States Patent
Feith et al.

(10) Patent No.: US 6,364,861 B1
(45) Date of Patent: *Apr. 2, 2002

(54) MULTI-VALVE INJECTION/ASPIRATION MANIFOLD

(75) Inventors: Raymond P. Feith, Rialto; Tim Truitt, Orange; Gary S. Werschmidt, Yorba Linda, all of CA (US)

(73) Assignee: Porex Medical Products, Inc., Ontario, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/154,939

(22) Filed: Sep. 17, 1998

(51) Int. Cl.$^7$ ................................................. A61M 5/00
(52) U.S. Cl. ........................ 604/247; 604/83; 137/512.4
(58) Field of Search ............................ 604/81, 86, 246, 604/247, 256, 250; 137/843, 854, 852, 853, 512.1, 493, 493.9, 512.4

(56) References Cited

U.S. PATENT DOCUMENTS

| | | | |
|---|---|---|---|
| 3,889,710 A | 6/1975 | Brost | |
| 3,954,121 A | 5/1976 | Kardos | |
| 4,141,379 A | 2/1979 | Manske | |
| 4,222,407 A | 9/1980 | Ruschke et al. | |
| 4,369,812 A | 1/1983 | Paradis et al. | |
| 4,556,086 A | 12/1985 | Raines | |
| 4,922,954 A | * 5/1990 | Blomquist et al. | ........ 137/512.4 |
| 4,946,448 A | * 8/1990 | Richmond | .................. 137/843 |
| 5,020,562 A | 6/1991 | Richmond et al. | |
| 5,205,834 A | * 4/1993 | Moorehead et al. | . 137/493.9 X |
| 5,431,185 A | * 7/1995 | Shannon et al. | ........ 604/247 X |
| 5,697,904 A | * 12/1997 | Raines et al. | ........... 604/247 X |

* cited by examiner

Primary Examiner—Anhtuan T. Nguyen
(74) Attorney, Agent, or Firm—Richard L. Myers; Myers, Dawes & Andras LLP (57) ABSTRACT

An IV manifold includes a plurality of injection/aspiration ports and has an elongate configuration with a width greater than the diameter of the ports. A flow channel is formed between mating members of a housing and provided with a U-shaped configuration. Projections along the flow channel direct fluid flow into valve cavities associated with the ports to clear dead spots around the valve elements. A check valve included in the manifold tends to direct high pressures against the valve elements which respond by forming surface seals thereby avoiding deformation. An aspiration port can be formed with a second seal disposed on the side of the valve element opposite the first seal. Opening this second seal by negative pressure in the lumen of the port provides for the aspiration of fluids in the flow channel. Two-way aspiration can be provided by a valve having a cage with or without compressible characteristics to accommodate low tolerance fittings.

25 Claims, 9 Drawing Sheets

MULTI-VALVE INJECTION/ASPIRATION MANIFOLD

BACKGROUND OF THE INVENTION

1. Field of the Invention

This invention relates generally to ports for injecting fluids into an intravenous (IV) line, and more specifically to injection manifolds including multiple injection ports.

2. Discussion of the Prior Art

Patients are commonly injected with IV solutions which are initially provided in a bottle or bag and dripped into the vein of the patient through an IV line. Typically an injection port is provided along the line and adapted to function with a syringe to permit an injectate to be added to the IV solution. If a large quantity of injectate, or multiple injectates, are to be added to the IV solution, multiple ports may be required. In such a case, an injection manifold can be disposed in the IV line to provide multiple injectate ports.

A check valve is also commonly included in the IV line where it is disposed upstream from the injection manifold. It is the purpose of the check valve to permit fluid flow only in the direction of the patient. This ensures that the injectate flows downstream toward the patient, not upstream toward the IV reservoir.

In the past, IV manifolds have been provided with an elongate and generally flat configuration in order to facilitate use of the multiple injection ports. The flow channel through the manifold has also had this elongate wide configuration, and consequently, has been susceptible to the formation of air pockets and to generally uneven flow characteristics. In the vicinity of the injection ports, the manifolds of the past have also developed dead spaces where the injectate has tended to collect rather than mix with the IV solution. Other IV manifolds have been provided with a round tube defing the flow channel. Injection ports have been connected to this tube at a "T" junction. In this case, the flow channel has reamined separate and the problems with dead spaces in the ports have been significant.

Injection ports of the past have generally included only valves with a single valve seal. These seals have not been capable of withstanding high pressure such as those sometimes associated with an injection into an adjacent port. The resulting high back pressure has sometimes caused the valve element to deform and lodge in the lumen of the port, rendering the port inoperative.

In the past, the ports associated with injection manifold have not been provided with characteristics permitting the aspiration of fluids from the flow channel. This is sometimes desirable in order to remove air from the manifold or withdraw a blood sample. In these cases, a separate aspiration port has been required in addition to the injection manifold.

Some injection ports have been provided with operative cages which mechanically open the valves. In this case a syringe having a male Luer fitting is relied on to push the cage against the valve element in order to open the valve. Due to wide tolerance variations in the plastic parts associated with the syringes, the male Luer fittings can sometimes extend into the injection port a distance greater than that required to open the valve. In many of these cases, damage to the injection port has resulted.

SUMMARY OF THE INVENTION

These problems with the injection ports and manifolds of the prior art are overcome with the present invention which provides for a generally U-shaped flow channel that extends axially of the manifold. By restricting the IV solution to this flow channel, the flow characteristics through the manifold are greatly enhanced. Importantly, there are no dead spots in the fluid flow through the manifold. Furthermore, the flow of fluid can be directed against the valve element of the injection port to avoid dead spots around the valve. A check valve can be included in this manifold and disposed at one end of the elongate housing. An infusion/aspiration port is preferably disposed upstream of the other injection ports and downstream of the check valve.

A preferred injection port is provided with two seals, a line seal and a surface seal, which provide for low pressure and high pressure operation, respectively. When an injectate is being introduced into an adjacent port, the resulting high back pressure is resisted by the high pressure surface seal of the port.

In an injection port embodiment including a cage, the cage can be configured to be axially compressible. These compressible characteristics accommodate the wide tolerance variations in the plastic parts which sometimes tend to cause a male Luer fitting to extend into the injection port a distance greater than that necessary to open the associated valve. By providing the cage with these compressible characteristics, the tolerance variations are accommodated without damaging the valve element.

In one aspect, the invention includes an injection port adapted for use with an IV line. The port includes a housing defining a flow channel and having an injection lumen. First portions of the housing define a first valve seat, while second portions of the housing define a second valve seat. A valve element, disposed to extend transverse to the injection lumen has properties for forming a first seal with the first valve seat at a first pressure, and a second seal with the second valve seat at a second pressure greater than the first pressure. The first valve seat, which forms part of the second valve seat, has the shape of a continuous line, while the second valve seat has the shape of a continuous surface.

In another aspect, the invention includes a port for injecting an injectate into a flow channel for aspirating a fluid from the flow channel. The port includes a housing defining the flow channel and having a lumen disposed in fluid communication with the flow channel. First portions of the housing define a first valve seat while second portions of the housing define a second valve seat. A valve element has properties for forming a first seal with the first valve seat and a second seal with the second valve seat when the valve element is in a natural state. The valve element has properties for opening the first seal in response to a positive pressure in the lumen to facilitate flow of an injectate into the flow channel. The valve element also has properties for opening the second seal in response to a negative pressure in the lumen in order to facilitate flow of the fluid from the flow channel into the lumen of the port. The first valve seat is formed on the side of the valve element opposite the flow channel. The second valve seat is formed on the side of valve element opposite the first valve seat. This embodiment may include a post with the second seal being formed around the post.

In an additional aspect of the invention an injection manifold includes a first body member and second body member forming a housing. First portions of the housing define a flow channel adapted to receive an IV solution flowing in an IV line. Second portions of the housing define at least one port with an injection lumen, the port having a outside diameter. The first portions of the housing have a width greater than the outside diameter of the port and define the flow channel with a width less than the diameter of the port. The flow channel will typically have a U-shaped configuration.

In a further aspect of the invention an injection/aspiration port includes a housing with first portions defining a flow channel and second portions defining an injection/aspiration lumen. Third portions of the housing define a valve seat around the lumen. A valve element is biased toward the injection/aspiration lumen and forms a seal with the valve seat. A valve cage is disposed in the lumen and adapted to be moved by insertion of a male Luer fitting into the lumen against the valve element to open the seal and permit two-way flow between the lumen and the flow channel. The valve cage is axially compressible to accommodate slight variations in the size of the male Luer fitting.

These and other features and advantages of the present invention will be more apparent with a description of preferred embodiments and reference to the associated drawings.

DESCRIPTION OF THE DRAWINGS

FIGS. 14–16 are cross-section views similar to FIG. 12 illustrating operation of an injection port which also has aspiration characteristics;

FIGS. 17 and 18 are cross-section views similar to FIG. 12 and illustrating a further embodiment including a mechanical cage for actuating the valve element;

DESCRIPTION OF THE PREFERRED EMBODIMENTS AND BEST MODE OF THE INVENTION

Figure 1:
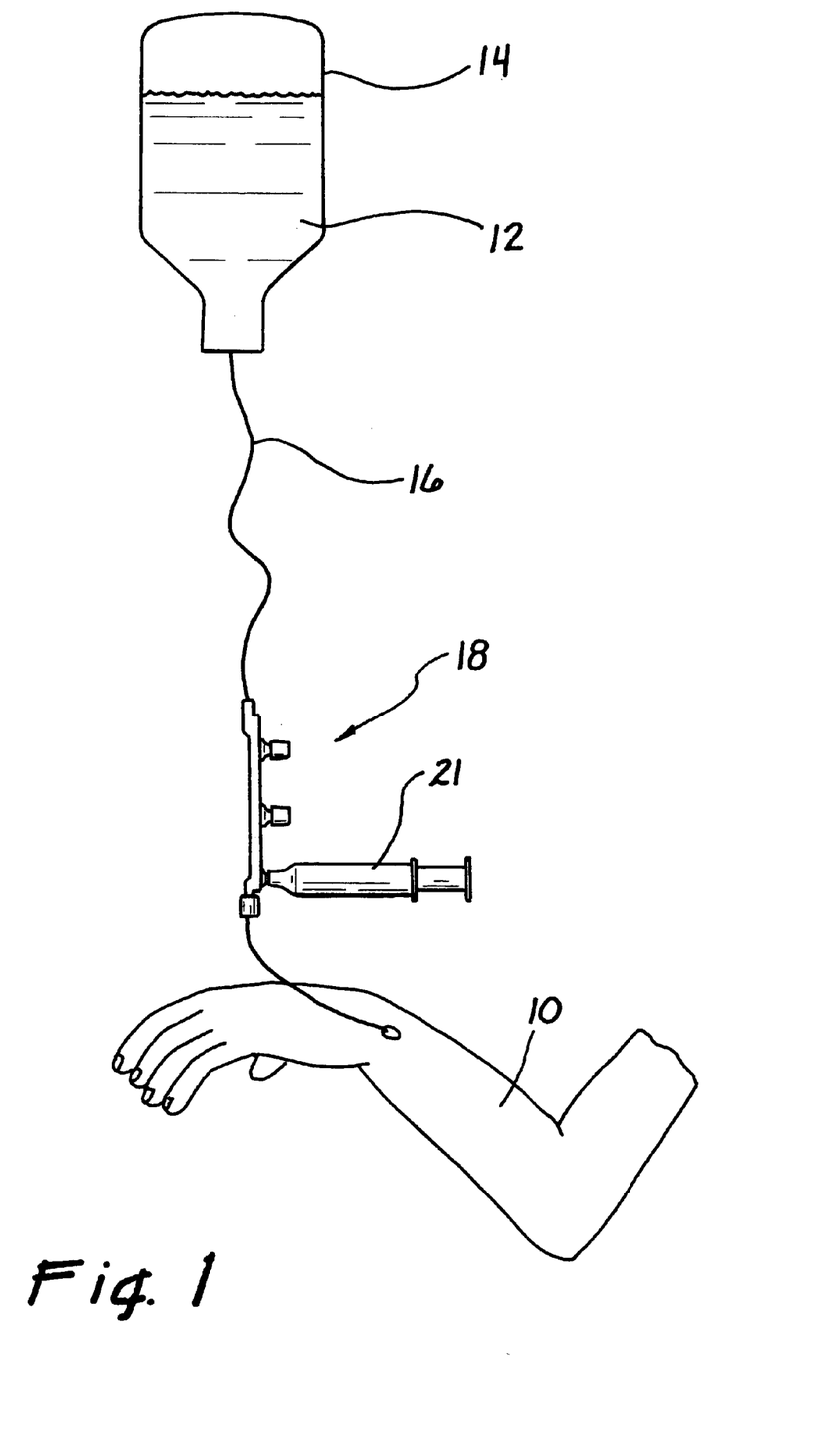
FIG. 1 is a perspective view of an arm of a patient with an IV solution appropriately administered through an injection manifold of the present invention.

The arm and hand of a patient are illustrated in FIG. 1 and designated generally by the reference numeral 10. An IV solution 12 contained in a reservoir, such as a bottle or bag 14, is appropriately communicated to the patient 10 through an IV line 16. An injection manifold 18 of the present invention is connected in series with the line 16 and provides a site where drugs and other fluids can be injected, typically through a syringe 21, into the IV solution in the line 16.

Figure 2:
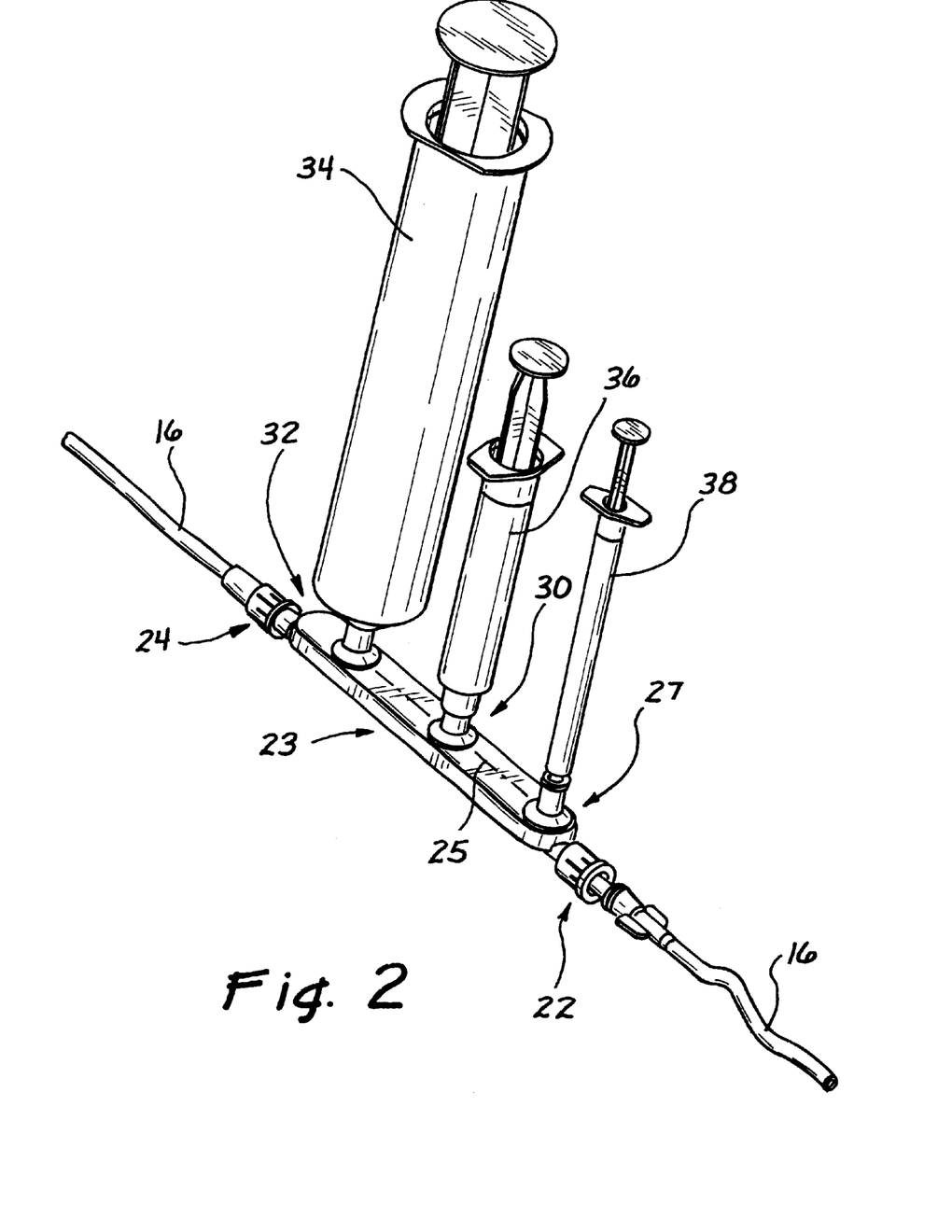
FIG. 2 is a perspective view of the manifold having three injection ports and syringes of various sizes connected to the ports.

The manifold 18 of a preferred embodiment is illustrated in greater detail in FIG. 2. In this view it can be seen that the manifold 18 has a housing 23 with an elongate configuration, and extends generally along an axis 25. The housing 23 is connected in series with the IV line 16, for example by a pair of connectors 22 and 24, so that the flow channel and the IV line 16 also extends through the housing 23.

A plurality of injection ports 27, 30 and 32 can be molded integrally with the housing 23 and spaced along the length of the housing 23. In FIG. 2, a 60 mm syringe 34 is connected to the port 32, while a 10 mm syringe 36 and a 5 mm syringe 38 are connected to the ports 30 and 27, respectively. There will of course be situations requiring three syringes such as the 60 cc syringe 34 that must be coupled to the manifold 18 at the same time. This will require that the ports 27, 30 and 32 be spaced sufficiently that the ports 27 and 32 are separated by a distance equal to two times the diameter of the 60 cc syringe 34, and the center port 30 disposed intermediate with the outer ports 27 and 32.

Figure 3:
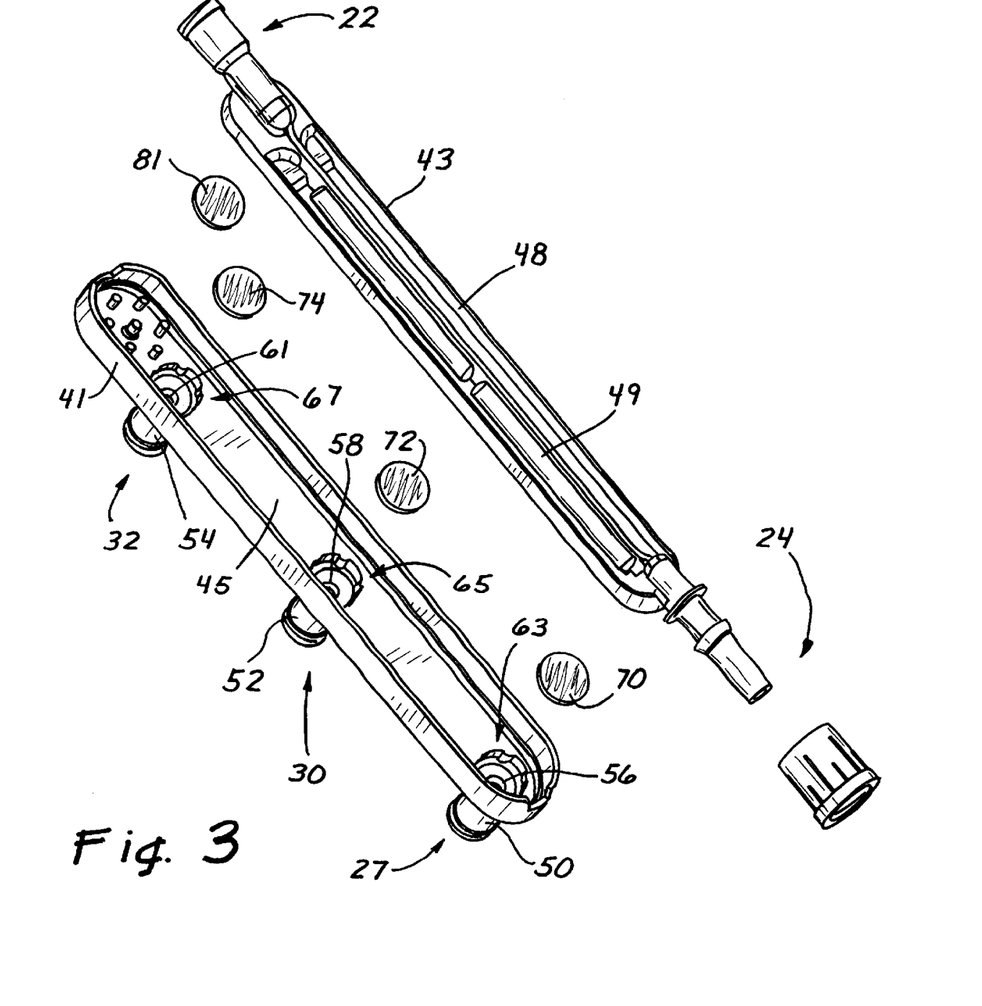
FIG. 3 is an exploded view of the manifold illustrating first and second members forming a housing, and showing the interior of the first member and the exterior of the second member.
Figure 4:
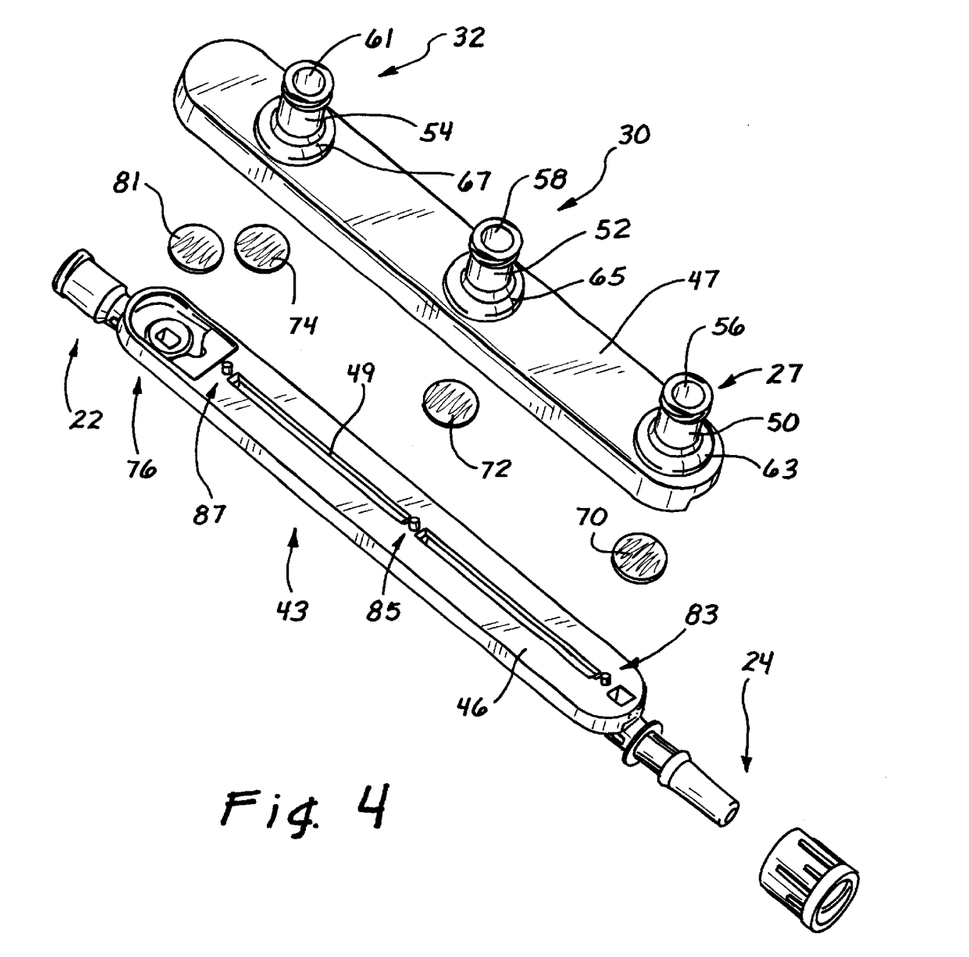
FIG. 4 is an exploded perspective view similar to FIG. 3 but showing the interior of the second member and exterior of the first member.
Figure 5:
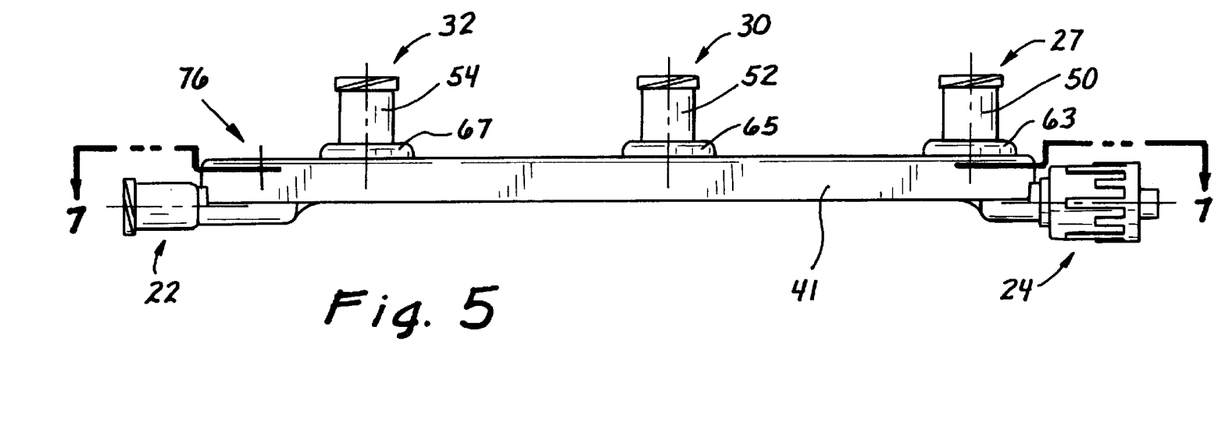
FIG. 5 is a side elevation view of the manifold illustrated in FIG. 2.
Figure 6:
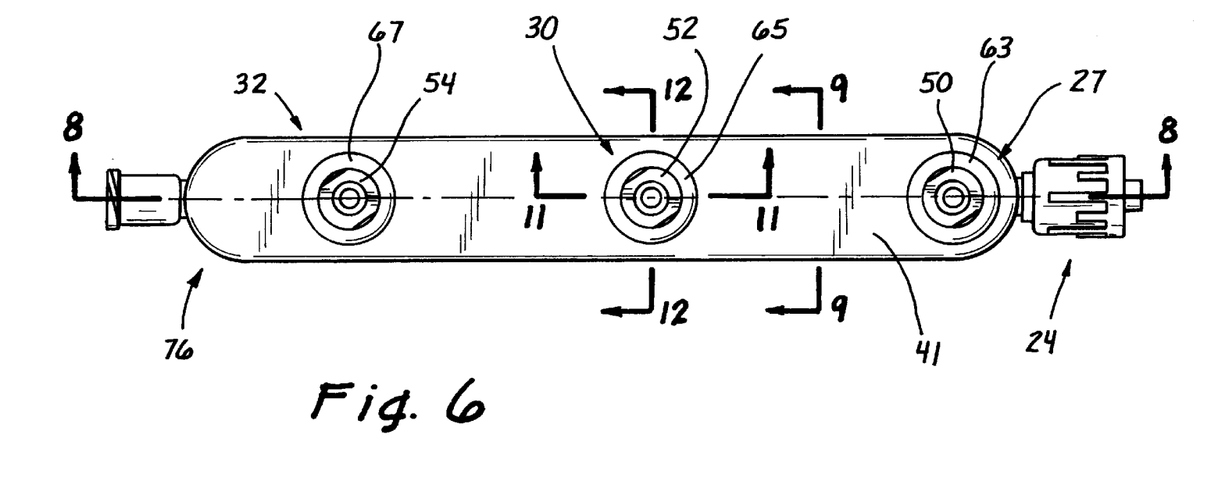
FIG. 6 is a top plan view of the manifold illustrated in FIG. 5.

The manifold 18 is further illustrated in the exploded views of FIGS. 3 and 4. In these views, the housing of a preferred embodiment is illustrated to include a first housing member 41 and a second housing member 43. The first housing member 41 has in inner side 45 illustrated in FIG. 3 and an outer side 47 illustrated in FIG. 4. Similarly, the second housing member 43 has an inner side 46 and an outer side 48. From these views it can be seen that each of ports 27, 30 and 32 includes a cylinder 50, 52 and 54, respectively, which projects from the outer surface 47 of the first housing member 41. These cylinders 50, 52 and 54 in turn define lumen 56, 58 and 61, respectively, which are in fluid communication with the flow channel 49. The cylinders 50, 52 and 54 also form with the first housing member 41 a plurality of cavities 63, 65 and 67, respectively, which are adapted to receive associated valve elements 70, 72 and 74. The operation of these ports 27, 30 and 32 will be discussed in greater detail below.

In this particular embodiment, a check valve 76 is provided at one end of the manifold 18. In this case, the check valve 76 is formed with a plurality of pins 78 which extend from the inner side 45 in a generally circular configuration. These pins 78 are adapted to receive a valve element 81. The manifold 18 is intended to be connected in the IV line 16 and oriented with the check valve 76 connected to the upstream side of the line 16.

Figure 7:
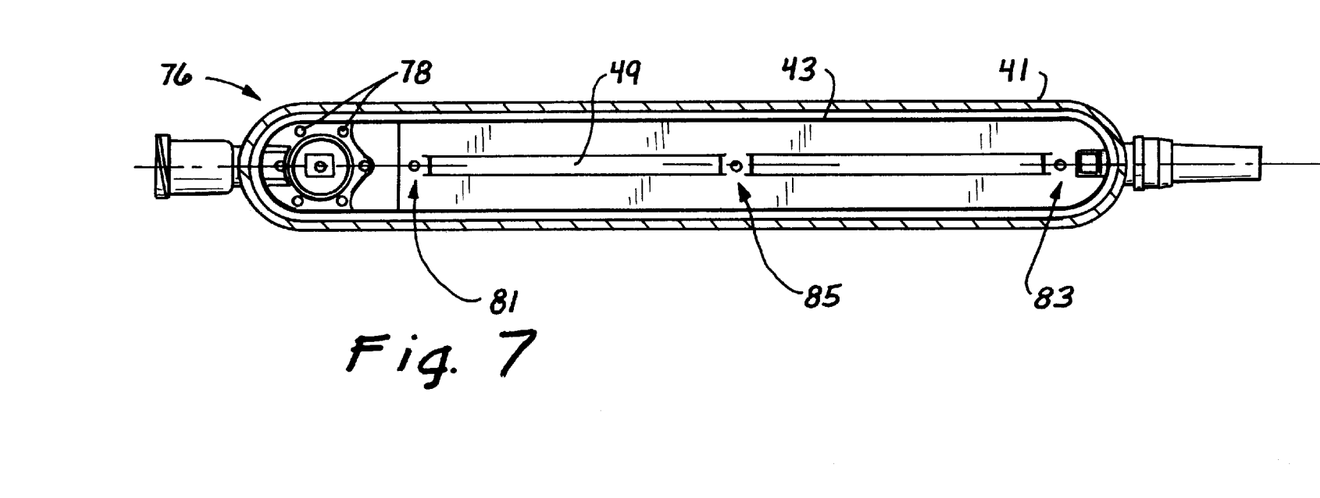
FIG. 7 is a cross-section view taken along lines 7—7 of FIG. 5.
Figure 8:
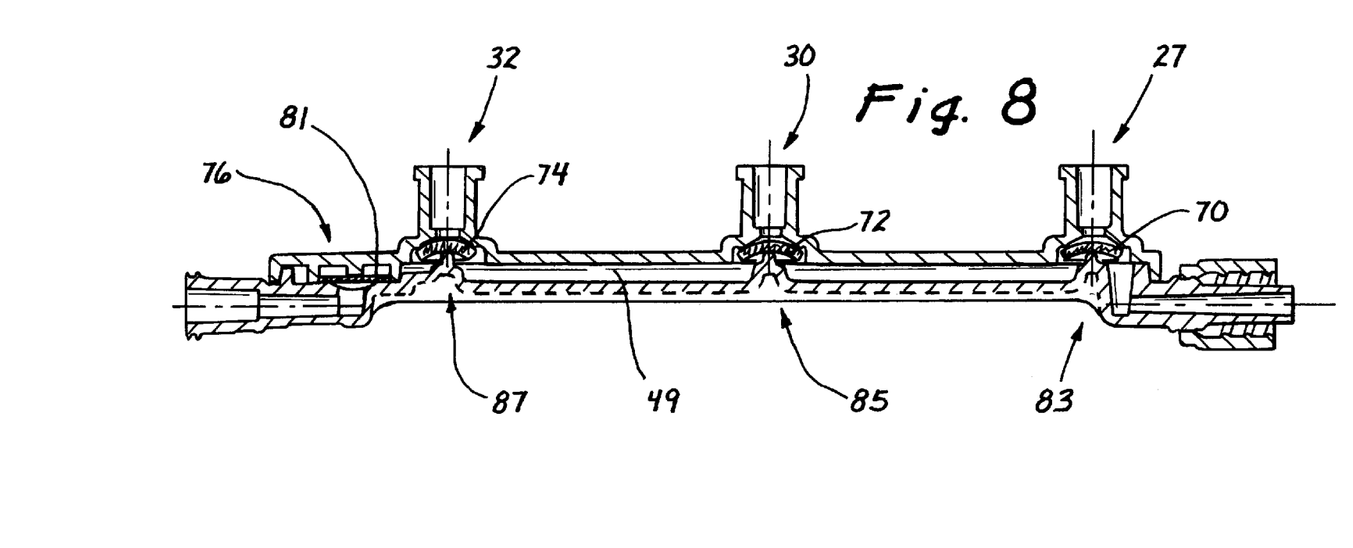
FIG. 8 is an axially cross-section view taken along lines 8—8 of FIG. 6.
Figure 11:
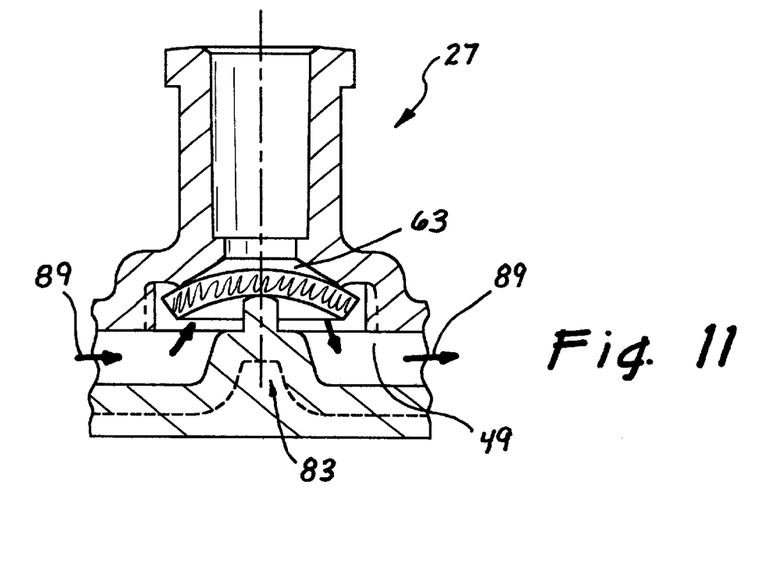
FIG. 11 is a radial cross-section view of an injection port taken along lines 11—11 of FIG. 6.

Perhaps best illustrated in FIG. 4 are a plurality of protrusions 83, 85 and 87 which interrupt the flow channel 49 at each of the associated ports 27, 30 and 32, respectively. These protrusions 83, 85 and 87, which are also illustrated in the assembled view of FIG. 7 and the cross-section view of FIG. 8, are of particular advantage to the present invention as they disrupt the flow of the IV solution 12 along the channel 49 and direct that flow into the associated cavities 63. With this directed fluid flow, the cavities 63, 65, and 67 particularly the valve elements 70, 72 and 74 are constantly washed so that there are substantially no dead spots associated with the injection ports 27, 30 and 32. In the past, these dead spots have been particularly common in the concave area beneath the valve 70, 72 and 74. With the fluid flow directed specifically onto the concave side of each element 70, 72 and 74 the dead spots are greatly minimized. This diverted flow is illustrated in greater detail in FIG. 11 where the cavity 63 and valve element 70 of the injection port 27 are washed by the IV solution flow which is illustrated by arrows 89.

Figure 9:
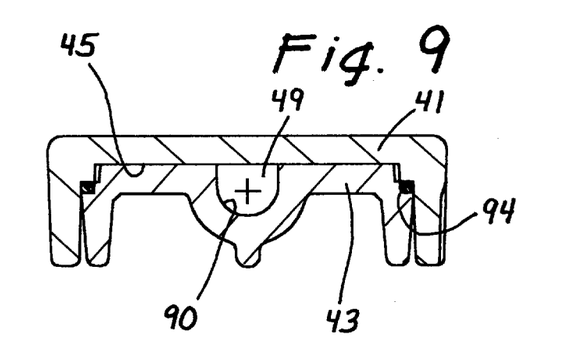
FIG. 9 is a cross-section view taken along lines 9—9 of FIG. 6.

With reference to FIG. 9, it can be seen that a preferred embodiment of the manifold 18 provides a flow channel 49 with a U-shaped configuration. This shape is generated by providing the inner surface 45 of the first housing member 41 with a generally planar configuration. When the second housing member 43 is mated to the first housing member 41, a U-shaped cavity 90 in the surface 48 automatically provides the flow channel 49 with the U-shape desired. In this particular embodiment, the generally planar inner surface of the housing member 41 makes it possible to also provide the outer surface 47 with a planar configuration. This shape greatly facilitates wiping the manifold 18 between the adjacent ports 27 and 30, and the ports 30 and 32.

Figure 10:
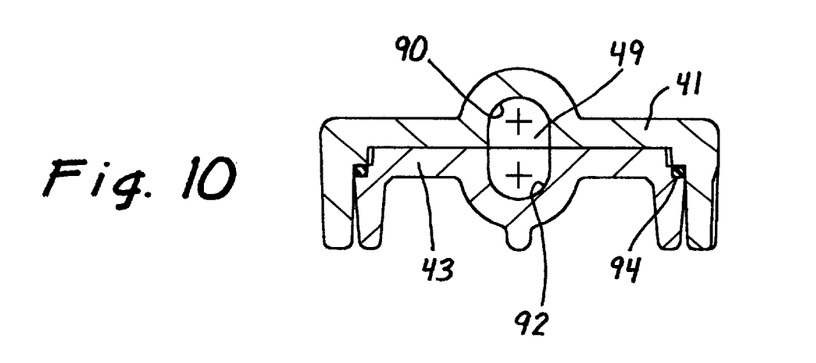
FIG. 10 is a cross-section view similar to FIG. 9 and illustrating a further embodiment of the manifold.

In an alternative embodiment illustrated in FIG. 10, the flow channel 49 is formed by the U-shaped cavity 90 formed in the first housing member 41, and by a second U-shape cavity 92 formed in the second housing member 43. When these parts are joined, the two cavities 90 and 92 provide the flow channel 49 with a shape of an oval. The views presented by FIGS. 9 and 10 also are best suited to illustrate the mating relationship of the first housing member 41 and the second housing member 43. These members 41 and 43 are operatively positioned with their respective surfaces 45 and 46 in close proximity so that these surfaces do not form any part of the flow channel 49. This contributes greatly to the flow characteristics within the channel 49 and avoids many of the air pockets and dead spots associated with the full-width flow channels of the prior art. The second housing member 43 can be fixed to the first housing member 41 in this operative position by means of adhesive or by heat seals 94.

Operation of the injection port 27 is best described with reference to FIGS. 12 and 13. In these views, it will be noted that the port 27 includes portions 96 which define a first valve seat and portions 98 which define a second valve seat. The first valve seat 96 forms a slight annulus above the valve element 70. In its normal configuration, the valve element 70, which has elastomeric properties, is biased by the protrusion 83 beneath the element 70 to form a seal with the first valve seat 96.

When an injectate is introduced through one of the adjacent ports, such as port 30 or 32, a relatively high pressure occurs in the flow channel 49. By operation of the check valve 76, this pressure is exerted against the underside of the valve element 70 of the port 27. In the manifold 18, the higher pressure will cause the valve element 70 to deform as illustrated in FIG. 13 until it comes into contact with the second valve seat 98 as illustrated in FIG. 13. With this second valve seat 98 providing surface contact with the valve element 70, a high pressure seal is formed without radical deformation or damage to the valve element 70.

Under some circumstances, it is desirable to have an injection port, such as the port 32, function not only to receive injectate into the flow channel 49, but also to aspirate or withdraw fluid from the flow channel 49. When an injection/aspiration port, such as the port 32, is included in the manifold 18, it is preferably disposed on the upstream side of the other ports so that injectate introduced in the other ports is not aspirated from the manifold 18. Since the check valve 76 is also to be positioned upstream of the ports 27, 29 and 32, it is desirable that the injection/aspiration port 32 be positioned next to the check valve 76.

Figures 14, 15, 16, 17:
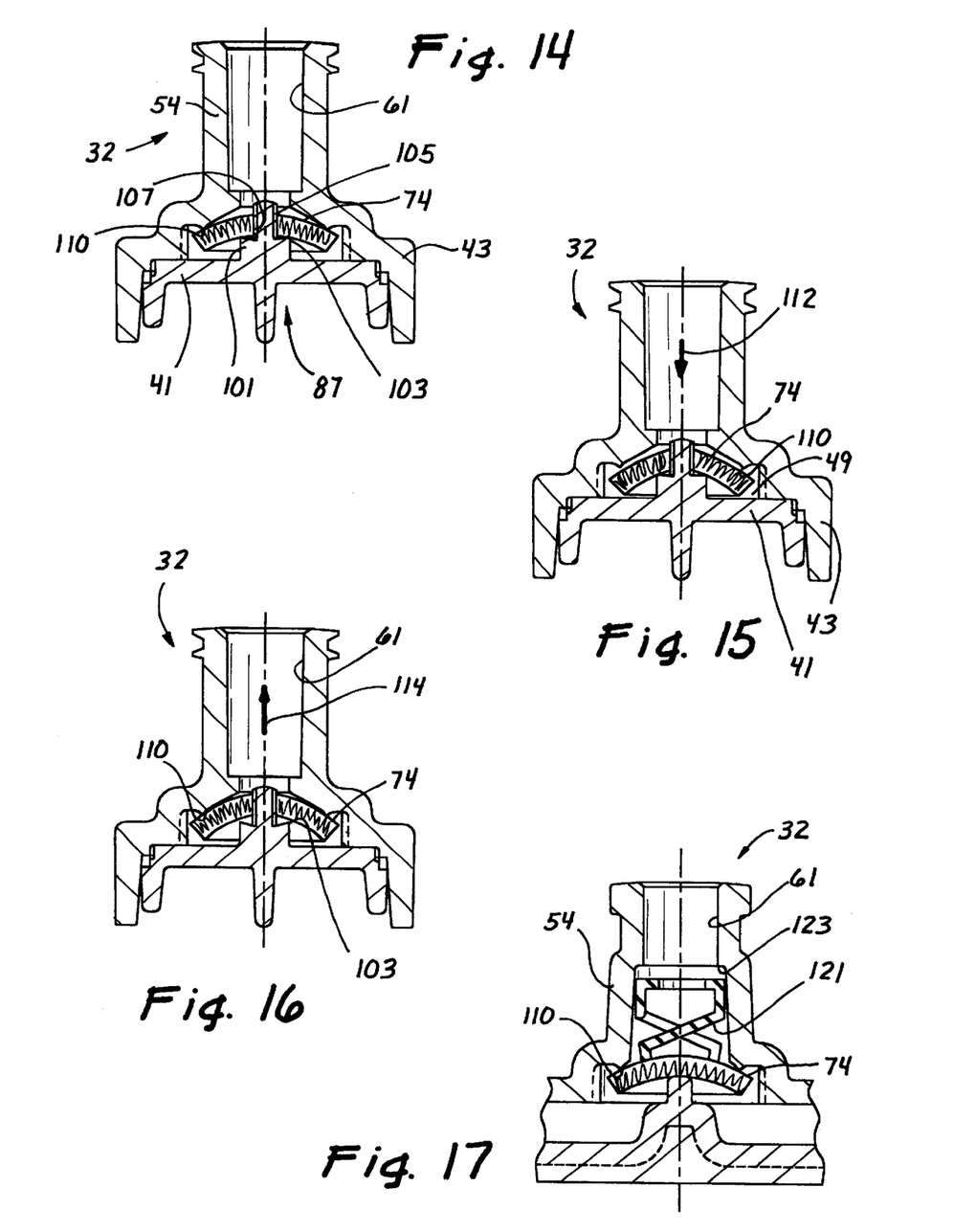
FIG. 14 is a cross-section view similar to FIG. 12 and showing a further embodiment of the invention with a valve in a normal state.
FIG. 15 is a cross-section view similar to FIG. 14 and illustrating the valve in an injection state.
FIG. 16 is a cross-section view similar to FIG. 14 and illustrating the valve in an aspiration state.
FIG. 17 is a cross-section view similar to FIG. 12 and showing the valve in a normal sealed state.

A preferred configuration for the injection/aspiration port 32 is illustrated in FIGS. 14–16. In this embodiment, the projection 87 is configured with a shoulder 101 which forms third valve seat 103, and a post extending toward the lumen 61 of the port 32. In this case, the valve element 74 is provided with a central aperture or hole 107 which is sized to receive the post 105. In the manner previously discussed with reference to the FIG. 12 embodiment, a first linear valve seat 110 can be formed above the valve elements 74 with the third valve seat 103 formed beneath the valve element 74. In its normal state, the port 32 is positioned with the valve element 74, biased to form a first seal with the first valve seat 110 and a second seal with third valve seat 103 as illustrated in FIG. 14. Under the fluid pressure of an injectate, as illustrated by an arrow 112 in FIG. 15, the valve element 74 is bent downwardly opening the first seal at the first valve seat 110. The second seal with the valve seat 103 is strengthened by this downward pressure against the valve element 74. Nevertheless, the injectate 112 flows through the first valve and into the flow channel 49.

Aspiration is accommodated by applying a suction to the lumen 61 as illustrated by an arrow 114 in FIG. 16. This causes the valve element 74 to raise off of the shoulder 103 which form the second valve seat. Fluid within the flow channel 49 is thereby permitted to pass between the valve element 74 and the post 105 into the lumen 61. In all cases, the hole 107 in the valve element 74, and the post 105, maintain the valve element 74 centered with respect to the valve seats 110 and 103, respectively.

Figures 12, 13, 18:
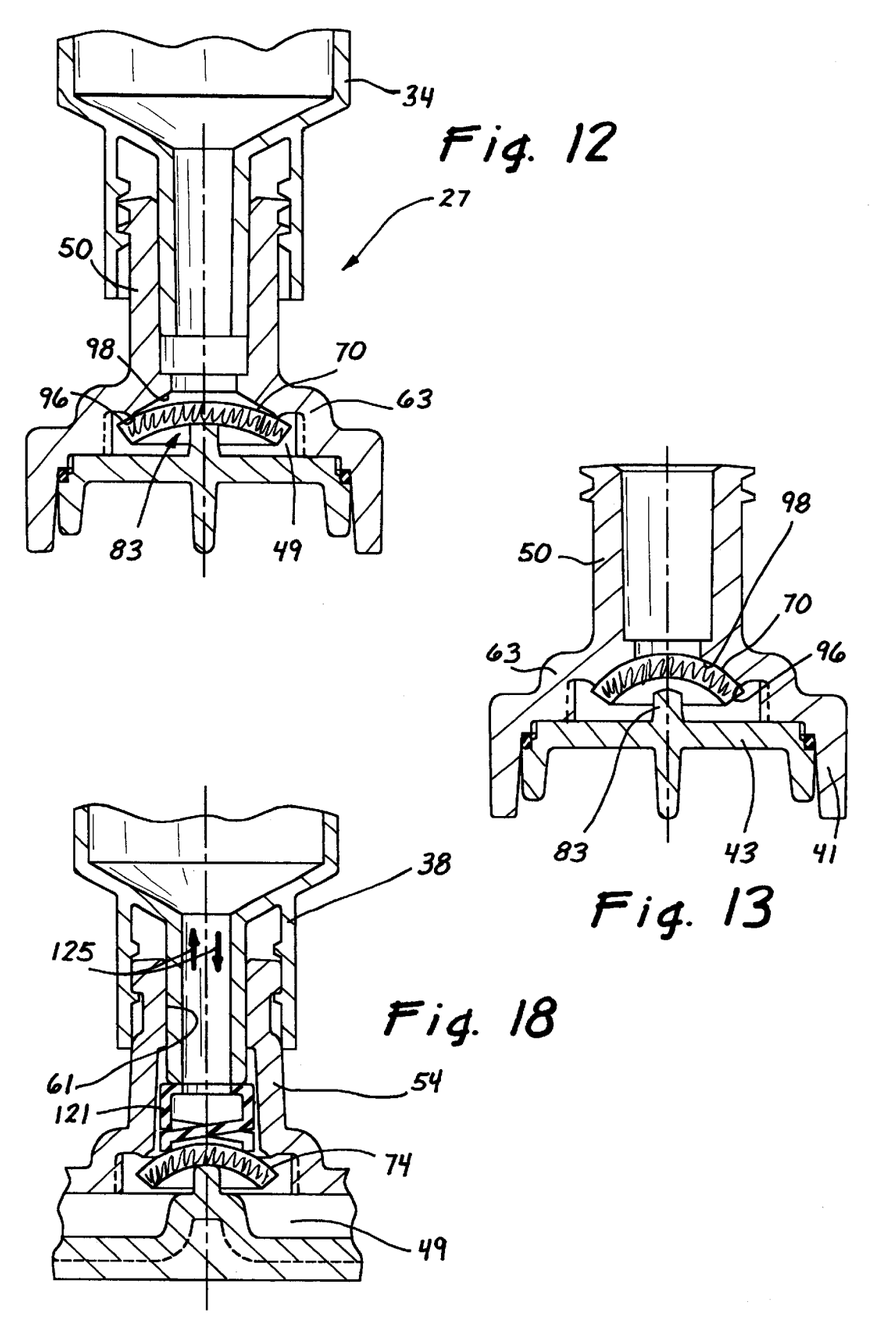
FIG. 12 is a radial cross-section view of the injection port taken along lines 12—12 of FIG. 6.
FIG. 13 is a cross-section view illustrating the port of FIG. 12 in a high pressure configuration.
FIG. 18 is a cross-section view similar to FIG. 17 and illustrating the cage in a compressed configuration with the valve in an injection/aspiration state.

A further embodiment of the injection/aspiration port 32 is illustrated in FIGS. 17 and 18. In this case, the port 32 is operated not by fluid pressure, but rather mechanically by the force of the syringe 38 acting upon a cage 121. In this case, the cylinder 54 defining the lumen 61 is provided with an interior shoulder which faces downwardly and prevents the cage 121 from moving upwardly within the lumen 61. In this embodiment, the cage 121 fits between the shoulder 123 of the cylinder 54 and the upper surface of the valve element 74. The cage 121 can be formed of wire or other resilient material and provided with a configuration which is axially compressible. The advantage of this port 32 is that it does not rely upon fluid pressure to open, but rather the mechanical force of a male Luer fitting 123 associated with the syringe 38.

With the tolerances accommodated in forming the Luer fitting 123 and in forming the lumen 61, it can be appreciated that the syringe 38 can extend a variable distance into the cylinder 54. If the cage 121 is provided only as a rigid element, damage to the valve element 74 can result when the male Luer fitting 123 extends too far into the lumen 61. In the illustrated embodiment, wherein the cage 121 is axially compressible, this great variation in distance of insertion can be accommodated by the cage 121 so that the valve element 74 is not radically deformed. When the valve element 74 is opened by the cage 121, two-way flow through the port 32 can be accommodated as illustrated by the arrows 125 in FIG. 18. Thus, the valve element 74 is separated from the valve seat 110 opening the valve to either receive injectate into the flow channel 49 or remove fluid from the flow channel 49.

It will be appreciated that many variations of these embodiments will now be apparent to those skilled in the art. Certainly, the configuration of the flow channel 49 can be varied widely to accommodate and improve fluid flow through the manifold 18. Also, the shape of the projections 83, 85 and 87 can be varied considerably as long as the fluid flow is directed into the cavities containing the valve elements. Other embodiments providing multiple valve seats to accommodate high and low pressures will also be apparent. In addition, other ports facilitating aspiration from the flow channel 49 will also be apparent to either provide two-way fluid communication, as with the embodiment of FIG. 7, or alternatively direct the fluid flow as illustrated in the embodiment of FIG. 14.

Based on these and many other variation which will now be apparent, one is cautioned not to determine the extent of the concept only with reference to the disclosed and illustrated embodiments, but rather to determine the scope of the invention only with reference to the following claims.

What is claimed is:

1. An injection port adapted for use with an intravenous line, comprising:
    a housing defining a flow channel and having an injection lumen extending in fluid communication with the flow channel;
    first portions of the housing defining a first valve seat around the injection lumen;
    second portions of the housing defining a second valve seat around the injection lumen;
    a valve element disposed to extend transverse to the injection lumen;
    the valve element having properties for forming a first seal with the first valve seat at a first fluid pressure; and
    the valve element having properties for forming a second seal with the second valve seat in addition to the first seal in response to a second fluid pressure greater than the first fluid pressure of the fluid in the flow channel.

2. The injection port recited in claim 1, wherein the first seal has the general shape of a continuous line extending around the injection lumen.

3. The injection port recited in claim 2, wherein the second seal has the general shape of a continuous surface extending around the injection lumen.

4. The injection port recited in claim 3, wherein the continuous line of the first seal forms part of the continuous surface of the second seal.

5. The injection port recited in claim 1, further comprising:
    third portions of the housing defining a third valve seat on the side of the valve element opposite the first and second valve seats; and
    the valve element having properties for forming a third seal with the third valve seat.

6. The injection port recited in claim 5, wherein:
    the valve element has properties for opening at least the first seal under the pressure of an injectate in the injection lumen to create a flow path around the valve element between the injection lumen and the flow channel; and
    the valve element has properties for opening the third seal in response to a partial vacuum in the injection lumen to aspirate a portion of the fluid in the flow channel around the valve element and into the injection lumen.

7. A port for injecting an injectate into a flow channel and for aspirating a fluid from the flow channel, comprising:
    a housing defining the flow channel and having a lumen disposed in fluid communication with the flow channel;
    first portions of the housing defining a first valve seat;
    second portions of the housing defining a second valve seat;
    a valve element disposed in the housing and having properties for forming a first seal with the first valve seat and a second seal with the second valve seat when the valve element is in a natural state;
    the valve element having properties for opening the first seal in response to a positive pressure in the lumen of the housing to facilitate flow of the injectate from the lumen to the flow channel; and
    the valve element having properties for opening the second seal in response to a negative pressure in the lumen to facilitate flow of the fluid from the flow channel into the lumen of the port.

8. The port recited in claim 7, wherein:
    the first valve seat is formed on the side of the valve element opposite the flow channel; and
    the second valve seat is formed on the side of the valve element opposite the first valve seat.

9. The port recited in claim 8, where:
    the first valve seat has the general shape of a circle with a first diameter; and
    the second valve seat is coaxial with the first valve seat and has the general shape of a circle with a second diameter less than the first diameter.

10. The port recited in claim 7, further comprising:
    third portions of the housing defining a post extending coaxially with the lumen; and
    the valve element includes portions defining a hole sized and configured to receive the post of the housing, and to form the second seal around the post.

11. The port recited in claim 10, wherein the post is tapered with progressive positions outwardly of the flow channel.

12. An injection manifold adapted to be disposed in an intravenous line extending from an intravenous reservoir to a patient, the manifold comprising:
    a first body member;
    a second body member forming with the first body member a housing;
    first portions of the housing defining a flow channel to receive the IV solution flowing in the IV line;
    second portions of the housing defining at least one port with an injection lumen extending in fluid communication with the flow channel, the port having an outside diameter; and
    the first portions of the housing defining a cavity with a width greater than the outside diameter of the port and defining the flow channel in proximity to the port with a width less than the outside diameter of the port.

13. The injection manifold recited in claim 12, wherein the housing has a generally flat configuration and extends longitudinally along an axis with the width of the cavity and the width of the flow channel extending transverse of the axis.

14. The manifold recited in claim 12, wherein:

the port is a first port and the second portions of the housing define a second port and a third port;

the second port is disposed intermediate the first port and the third port and the first and third ports are spaced a distance greater than twice the diameter of a 60 cc syringe.

15. The injection manifold recited in claim 12, wherein the flow channel is U-shaped in radial cross section.

16. The injection manifold recited in claim 12, wherein the first body member includes first portions and the second body member includes second portions which define the flow channel with the first portions of the first body member;

the first portions of the first body member having a generally straight configuration in radial cross section and the second portions of the second body member having a generally rounded configuration in radial cross section.

17. The injection manifold recited in claim 12, wherein the first body member has an outer surface with a generally planer configuration between the first port and the second port to facilitate wiping the outer surface of the manifold between the injection ports.

18. The injection manifold recited in claim 14, wherein each of the first port, the second port, and the third port include an associated valve element, and the valve elements are disposed generally in a common plane.

19. The injection manifold recited in claim 14, wherein the second port is disposed between the first port and the third port, and the manifold further comprises:

a check valve disposed on the side of the first port opposite the second port.

20. The injection manifold recited in claim 19, wherein the first port has properties facilitating the injection of fluids into the flow channel and the aspiration of fluids from the flow channel.

21. An injection/aspiration port adapted for operation with a male Luer fitting, comprising:

a housing;

first portions of the housing defining a flow channel;

second portions of the housing defining an injection/aspiration lumen;

third portions of the housing defining a valve seat around the injection/aspiration lumen;

a valve element biased toward the injection/aspiration lumen and forming a seal with the valve seat;

a spring-biased valve cage disposed in the lumen and adapted to be compressed by insertion of the male Luer fitting into the lumen against the valve element to open the seal and permit two-way flow between the lumen and the flow channel.

22. The injection/aspiration port recited in claim 21, wherein the valve cage has an expanded state wherein the seal is closed and a compressed state wherein the seal is open, the cage being bias to the expanded state and being axially compressible by the male Luer fitting syringe to the compressed state.

23. The injection/aspiration port recited in claim 21, wherein the housing comprises:

a first body member defining the lumen and the valve seat;

a second body member forming the housing with the first body member and including portions contacting the valve element on the side of the valve element opposite the valve seat to force the valve element against the valve seat to form the seal.

24. The injection/aspiration port recited in claim 23 wherein the portions of the second body member comprise a post.

25. The injection/aspiration port recited in claim 21, wherein the valve cage is spring-biased to the expanded state.

* * * * *